United States Patent [19]

Anderson et al.

[11] Patent Number: 5,416,198
[45] Date of Patent: May 16, 1995

[54] SELECTIVE SORBENT REMOVAL SYSTEM USING POLYCATION ACTIVATED SUBSTRATES

[75] Inventors: Christopher G. Anderson, Salt Lake City; James C. McRea, Midvale, both of Utah

[73] Assignee: Research Medical, Inc., Midvale, Utah

[21] Appl. No.: 13,967

[22] Filed: Feb. 5, 1993

[51] Int. Cl.$^6$ .................... B01D 61/00; B01D 63/02; B01D 15/08; C07H 1/00
[52] U.S. Cl. .................................. 536/111; 210/644; 210/645; 210/649; 210/650; 210/651; 210/660; 210/661; 536/18.7; 536/124; 527/300; 527/312; 604/4; 604/5; 604/6
[58] Field of Search .............. 536/1.11, 18.7, 124; 527/300, 312; 604/4, 5, 6; 210/644, 645, 649, 650, 651, 660, 661

[56] References Cited

U.S. PATENT DOCUMENTS

| | | | |
|---|---|---|---|
| 4,062,882 | 12/1977 | Sen Gupta | 210/623 |
| 4,883,598 | 11/1989 | Riethorst et al. | 210/656 |
| 4,923,439 | 5/1990 | Seidel et al. | 604/6 |
| 4,968,432 | 11/1990 | Antwiler | 210/645 |
| 5,084,398 | 1/1992 | Huston et al. | 514/12 |
| 5,151,192 | 9/1992 | Matkovich et al. | 210/646 |
| 5,173,470 | 12/1992 | Bruening et al. | 210/670 |
| 5,183,872 | 2/1993 | Heidel et al. | 527/312 |
| 5,211,850 | 5/1993 | Shettigar et al. | 210/645 |

Primary Examiner—Ronald W. Griffin
Attorney, Agent, or Firm—Thorpe, North & Western

[57] ABSTRACT

A polycationic system for the removal of polyanions from a fluid medium is formed by, first, activating a biocompatible hydroxylated support with an organic sulfonyl chloride, such as p-toluene-sulfonyl chloride, in the presence of a dialkylamino pyridine activation catalyst, such as 4-dimethylamino-pyridine (DMAP). The activated support is then reacted with a polymer having a polyamide backbone with pendent alkyl amine groups, such as poly-L-lysine (PLL), to form C—N bonds between an activated carbon from the hydroxylated polymer and an amine group from the polymeric polyamide. Finally, any unreacted activated sites on the hydroxylated polymer are capped or removed with an effective amount of capping agent such as a mercapto (—SH), hydroxy (—OH) or amino (—NH$_2$) containing compound which reacts with the unreacted activated sites. The pendent alkyl amines on the polyamide backbone exist, at the appropriate pH, as polycations. The polyanion, such as heparin, is removed from fluids, such as blood plasma and whole blood, by bringing these fluids in contact with the polycationic system. The polyanion is bound to the polycation system by ionic attraction. The polyanion can then be released from the polycation system by treatment with a basic solution, thereby allowing the system to be reused.

42 Claims, No Drawings

SELECTIVE SORBENT REMOVAL SYSTEM USING POLYCATION ACTIVATED SUBSTRATES

This invention relates to a method of coupling a polymer containing a polyamide backbone with pendent alkyl amines to a hydroxylated or modified hydroxylated polymer and to the use of the pendent alkyl amines in removing polyanions from fluids. More particularly, this invention relates to a method of coupling a polymer containing a polyamide backbone with pendent alkyl amines to a polysaccharide or modified polysaccharide backbone polymer via amine catalyzed organic sulfonyl chloride activation chemistry followed by capping unreacted activating sulfonates or other activating agents to provide a pendent alkyl amine activated substrate having optimal cationic charges for the binding and removal of the polyanions.

BACKGROUND OF THE INVENTION

Separating particular materials from fluids that contain complex combinations of constituents has traditionally been a difficult and expensive task. The importance and feasibility of making such separations have increased to the point that a new branch of science, referred to as separation science, has been recognized. Polyanions are one class of materials for which satisfactory methods of separation are inadequate. For example, there is no adequate, biocompatible method of separating polyanions, such as heparin and certain blood coagulating protein factors like factor X, from blood or other fluids.

Heparin exists mainly in the lungs, intestine, and liver of a variety of mammals. Heparin is richly found intracellularly in mucosal mast cells, connective tissue mast cells and basophilic leukocytes. Commercial heparin preparations are mostly obtained from porcine intestinal mucosa or beef-lung. It is composed of alternating, 1-4 linked uronic acid and D-glucosamine. The uronic acid residues are either L-iduronic acid or D-glucuronic acid; D-Glucosamine residues are either N-sulfated (major proportion) or N-acetylated (minor proportion). Heparin is extremely heterogeneous in both structure and molecular weight because the biosynthesis of its precursors, heparinproteoglycans (M. W. 750,000 to 1,000,000), is usually not completed. Low molecular weight heparin refers to the fractionated or depolymerized heparin, which has a lower molecular weight than the normal commercial grade heparin.

The anticoagulant properties have been demonstrated to be associated with heparin binding to Antithrombin III (ATIII). ATIII is a plasma glycoprotein with molecular weight approximately 58,000. ATIII binds with thrombin very tightly at a 1:1 stoichiometric ratio, which blocks the active site on thrombin and prevents it from interacting with fibrinogen. However, the inhibition rate of thrombin with ATIII is low in absence of heparin. Heparin dramatically accelerates the rate of thrombin inactivation up to 2000-fold. Clinically used heparin can be separated into two distinct fractions according to its affinity for ATIII. Approximately 33% of heparin has a high affinity for ATIII, which has potent anticoagulant activity (up to 90% of the activity of the unfractionated heparin). A low-affinity heparin binds to the same site on ATIII, but with approximately 1000 times lower affinity.

Although anticoagulation is the major pharmacological activity, heparin has many other functions. Heparin inhibits the proliferation of vascular smooth muscle cells and renal mesengial cells, suppresses the delayed-type hypersensitivity, and inhibits angiogenesis. Other pharmacological functions of heparin include antithrombotic effect, antibacterial, antivirus, and antitumor angiogenesis, particularly in combination with cortisone. Although it has been clinically observed that heparin may induce thrombocytopenia, in vitro studies have shown that normal heparin enhances the release of platelets. Moreover, various heparin-binding growth factors can be purified with heparin affinity chromatography.

Heparin has been extensively used in many clinical applications, including cardiac surgery, peripheral vascular surgery, dialysis, autotransfusion, transplantation, the treatment of pulmonary embolism, disseminated intravascularcoagulation, and venous thrombosis. The dosage is dependent on the type of application. Heparin has also been used as a prophylactic agent against deep vein thrombosis. The dose of heparin for this treatment is relatively low, e.g., 10,000 U/24 hr for subcutaneous administration. Heparin is also of value in the treatment of thromboembolic disorders, such as pulmonary embolism and arterial thrombosis. These treatments require relatively high doses of heparin, approximately 30,000 U/24 hr.

As a polyanion, many properties and applications of heparin are associated with electrostatic interactions. Binding of negatively charged heparin onto polycationic surfaces has been applied in the biomedical field in two major ways.

One is heparin immobilized nonthrombogenic surfaces. As an anticoagulant, heparin has been fixed onto polymers with positive charges by forming a stable complex. The immobilized heparin on the surface is released into blood by ion exchange, subsequently, the released free heparin interacts with ATIII. Heparin was complexed with benzalkonium, bearing quaternary ammonium moiety, mixed with graphite, and developed as a graphite-benzalkonium chloride-heparin (GBH) surface in 1961. This surface showed a thrombogenic resistance, however, the heparin release rate was too high to be used in long term applications. Many other polycationic surfaces have been developed in order to ionically bind heparin strongly, thereby giving a lower heparin release rate. Although these heparin-immobilized biomaterials have shown an improved in vitro and in vivo hemocompatibility, there remains major unresolved problems, i.e. the high release rate of heparin and leakage of cationic reagents. To overcome these obstacles, polycations have been adapted to immobilize heparin. Poly(amido-amine) grafted 33polyurethane (PUPA), and polyvinylchloride grafted with both polyethyleneglycol monomethacrylate and quarternized dimethylaminoethyl methacrylate (Anthron) have shown good long term blood compatibility.

A second field of application relates to heparin neutralization. Excessive heparin in the blood can be attracted and thus removed by electrostatic interactions with polycationic surfaces.

From the above it is apparent that the same principle of heparin interaction with polycationic surfaces can be used for different purposes, i.e. to release heparin into the blood or remove heparin from the blood. In the case of heparinized nonthrombogenic surfaces, heparin electrolytically binds with the polycationic surface before contact with blood. When the heparinized surface is exposed to blood, the immobilized heparin undergoes sustained release from the surface. In contrast, in the case of the removal of heparin from blood, heparin is the blood at high concentrations before it contacts the polycationic surfaces. Heparin electrostatically binds with the polycationic surfaces after exposure to blood and thus is removed from the blood.

Because the high level of heparin for prolonged period of time is contraindicated, numerous efforts have been made to minimize the adverse effects of heparin in the blood. These approaches are diversified into at least three groups. One is the administration of protamine to neutralize the heparin effects. A second if the use of heparin derivatives as anticoagulants, such as low molecular weight heparin. A third is the minimization of the dose of heparin. Each one of these approaches has serious drawbacks.

Intravenous protamine administration often leads to adverse hemodynamic interactions and causes a sudden fall in blood pressure. In addition, cardiovascular suppression, system hypotension, pulmonary hypertension, anaphylaxis, and complement activation have also been reported after protamine administration. Moreover, a heparin rebound effect and consequent bleeding may occur hours after initial heparin neutralization by protamine. Therefore, the dose of protamine needs to be carefully chosen because insufficient neutralization may still induce hemorrhagic complications and overdose of protamine is also contraindicated. For these reasons the use of protamine for heparin neutralization is still very difficult.

The use of a low molecular weight heparin derivative is not as effective as an anticoagulant compared with high molecular weight heparin. Low molecular weight heparin loses its effectiveness more rapidly since it breaks down in the body more readily than high molecular weight heparin.

The administration of minimal doses of heparin is dangerous since this increases the likelihood of unwanted coagulation after surgery thus forming unwanted blood clots in the arteries and veins.

The level of heparin in whole blood and blood plasma both in vitro and in vivo is critical to the well-being of the patient. It has been a problem to remove heparin from whole blood and blood plasma. The present invention aids in the solution of these long-standing problems.

Factor X is a key blood clotting factor in human physiology. Blood coagulation occurs through a complex series of reactions known as the clotting or coagulation cascade. This cascade is regulated by a series of zymogen (inactive enzyme precursor) to enzyme conversions that ultimately results in polymerization of insoluble fibrin. This insoluble fibrin becomes cross-linked and, together with platelets and other components of the blood, forms a blood clot. There are two pathways, intrinsic and extrinsic, that make up the clotting cascade for blood coagulation. The intrinsic pathway is initiated by activation of blood factor XII while the extrinsic pathway is initiated by release of tissue thromboplastin after injury to blood vessels. The intrinsic and extrinsic pathways merge in a step of the cascade involving activation of factor X. Thus, factor X plays a key role in blood clotting because it is common to both blood clotting pathways and is the blood factor at the critical point where the two pathways join. After this merger of the two pathways, one series of reactions leads to formation of the insoluble fibrin.

Factor X is a protein that is synthesized in the liver and depends on vitamin K for its synthesis. An amino terminal domain of factor X contains several γ-carboxy-glutamic acid residues. Each of these modified glutamic acid residues contains an additional free carboxyl group, thus creating a highly negatively charged region in the protein. Thus, factor X is a polyanion and can be separated from fluids in a manner similar to that used for separating heparin.

DESCRIPTION OF PRIOR ART

Composed mainly of alternating D-glucosamine and L-iduronic acid, heparin exhibits a strongly negative charge at neutral pH. The electrostatic interactions between heparin and polycationic surfaces have been recognized to be of importance in biomedical applications. As stated above, these applications can be grouped into the two major areas of providing non-thrombogenic surfaces and heparin neutralization.

Non-thrombogenic surfaces. Since heparin is a potent anticoagulant, heparin-coated surfaces have been explored for development of nonthrombogenic materials. Polymers bearing positive charges, such as poly-4-vinylpyridine, Fourt et al., *Adv. Chemi. Ser.* 87, 187 (1968), poly(amidoamine) grafted polyurethane (PUPA), Azzuuoli et al.,*Biomaterials* 8, 61 (1987), and Anthron, Nagaoka et al.,*J. Biomater. Appl.* 4, 3 (1989), have been reported to form a stable complex with heparin and, consequently, have been used to anchor heparin onto surfaces.

Heparin neutralization. Excessive heparin in circulating blood needs to be neutralized after extracorporeal circulation due to the risk of hemorrhagic complications. Usually this is achieved by administration of protamine, a cationic protein, Anido et al., *Am. J. Clin. Pathol.* 76, 410 (1981). However, protamine also has undesirable side effects, including the risk of anaphylactic reactions in some patients. To circumvent this problem, protamine immobilized cellulose hollow fibers, Kim et al.,*Trans. Am. Soc. Artif. Intern. Organs,* 35, 644 (1989), and protamine grafted glycidyl methacrylate gel-cellulose, Hou et al., *Artif. Organs,* 14, 436 (1990), have been developed. In addition, other cationic polyelectrolyte surfaces have also been proposed for binding and thus removal of heparin, including the use of triethylaminoethyl cellulose powder (Heparsorb, Organon Teknika, Durham, N.C.) and poly(1-lysine)-Sepharose 4B, Mohammad et al., *Thromb. Res.,* 20, 599 (1980).

Numerous processes exist for activating hydroxyl carrying supports such as agarose, cellulose, diol-silica, glycophase-glass or hydroxyethyl methacrylate gels for reaction with proteinaceous materials, e.g. Dean, *Affinity Chromatography, A practical Approach,* IRL Press, Oxford, (1984); Cuatrecasas, U.S. Pat. No. 3,947,352, Mar. 30, 1976 and Hou et al., U.S. Pat. No. 4,663,163, May 5, 1987). Nilsson et al. *Eur. J. Biochem,* 112 397 (1980); Nilsson et al. *Acta. Chem. Scand. Ser. B.,* B35, 19(1981); Nilsson et al. *Biochem. Biophys. Res. Commun.,* 102, 449(1981); and Nilsson et al. *Methods in Enzymology,* 104, 56(1984) describe methods of coupling biomolecules, such as enzymes or other proteinaceous materials, to these activated hydroxyl containing supports. In the prior art, a preferred method of activating the hydroxyl carrying supports is the use of cyanogen bromide and the tresyl group (1,1,1-trifluroethanesulfonyl). In the literature cited above, the activation of pendant hydroxyl groups with p-toluenesulfonyl chloride (tosylation) has also been suggested as a means of activating the hydroxyl carrying supports. The use of the tosyl group with elevated temperatures for activation often causes irreversible damage or denaturization of the proteinaceous nucleophiles that are being coupled to the hydroxyl containing supports. Coupling of nondenaturable proteinaceous materials at elevated temperatures to tosylated polysaccharides occurs most often through an amino group to yield a carbon-nitrogen (C—N) bond. The resulting products are very stable.

The prior art referred to above describes the tosylation reaction as being carried out in the presence of pyridine as a catalyst for the reaction. Normally the unreacted tosyl groups are removed with a mercapto compound such as Tris-HCl buffer or mercaptoethanol.

It would be beneficial to provide a biocompatible substrate to which was firmly bonded significant amounts of a polycationic ligand for the removal of polyanions such as heparin and Factor X.

OBJECTS AND BRIEF SUMMARY OF THE INVENTION

It is an object of this invention to provide a means of removing polyanions from fluids, e.g. heparin from blood, by means of polycationic binding of the polyanions.

It is a further object of this invention to provide means of controlling the amount of polycations in a fluid such as heparin or Factor X in the bloodstream.

An additional object of this invention is the formation of certain hydroxylated polymeric substrates having bonded thereto, via a stable carbon-nitrogen bond, a polyamide backbone with pendent alkyl amines serving as polycations.

The polyanion removal or control system is formed by, first, activating a biocompatible hydroxylated support with an organic sulfonyl chloride in the presence of a dialkylamino pyridine activation catalyst. Then, the activated support is reacted with a polymer having a polyamide backbone with pendent alkyl amine groups to form C—N bonds between an activated carbon from the hydroxylated polymer and an amine group from the polymeric polyamide. Finally, any unreacted activated sites on the hydroxylated polymer are capped or removed with an effective amount of capping agent which effectively removes or neutralizes the activated sites of the hydroxylated polymer not reacted with the polyamide polymer.

More particularly, a biocompatible hydroxylated polymer support, cross linked or not, having sites which can form stable C—N bonds along the backbone is reacted with an organic sulfonyl chloride activating reagent in the presence of a dialkylamino pyridine activation catalyst. Hydroxyl carbons of the hydroxylated polymer support, activated by the presence of sulfonated groups, are then reacted with a biocompatible ligand polymer having a polyamide backbone with pendent alkyl amines having up to five carbon atoms on the pendent chain. From this reaction, C—N bonds are formed between the activated carbons of the polymer support and amine nitrogen atoms of the ligand polyamide polymer. However some activated sites remain unreacted with the polyamide ligand. The activated sites are capped or removed by the subsequent reaction with a capping agent such as a mercapto (—SH), hydroxy (—OH) or amino (—NH$_2$) containing compound which reacts with the unreacted activated sites.

The pendent alkyl amines on the polyamide backbone exist, at the appropriate pH, as polycations.

For example, using p-toluene-sulfonyl chloride (tosyl chloride or p-toluene-SO$_2$Cl) as the activating agent, 4-dimethylamino-pyridine (DMAP) as the activation catalyst, poly-L-lysine (PLL) as the ligand and cysteine (HS-Cys) as the capping agent the overall reaction may be represented by the following reaction sequence:

Activation:

Coupling:

Capping:

Unless otherwise specifically stated, the terms "polyanion", "heparin", "Factor X" and the like can be used interchangeably insofar as it pertains to the binding of these negatively charged ions to a polycationic substrate. Therefore, while the invention is primarily defined and described in terms of heparin, the use of heparin and blood or plasma to illustrate the invention is considered to be representative of the polyanions and fluids to which the invention is applicable.

Therefore, for purposes of illustration, heparin is removed from fluids such as blood plasma and whole blood by bringing these fluids in contact with the polycationic supports prepared as described above. Heparin, as a polyanion, is bound to the polycations by ionic attraction. Heparin can then be released from the support immobilized polycations by treatment with a basic solution, thereby allowing the material to be reused.

DETAILED DESCRIPTION AND PREFERRED EMBODIMENTS OF THE INVENTION

The invention as summarized above can be adapted to be inclusive of different hydroxylated supports, activated by a variety of alkyl or aryl sulfonyl chlorides catalyzed by dialkylaminopyridines for reaction with polyamide ligands made up of a polyamide backbone having pendent alkylamine sidechains and capped with suitable capping agent to remove activation sites unreacted by the polyamide ligands.

The purpose of the following disclosure is set forth the best mode presently known for carrying out the invention and described herein and claimed by the appended claims. However, one skilled in the art will be able, from this disclosure, to adapt the invention to embodiments not specifically disclosed but which are considered to be within the scope of the invention.

The hydroxylated polymers which may be used are any biocompatible polysaccharide or modified polysaccharide backbone polymers, which may or may not be crosslinked, having sites which can be activated and form stable C—N bonds along the polymer backbone. Illustrative of such polysaccharides are members selected from the group consisting of cellulose, reformed cellulose, regenerated cellulose, chitin, chitosan (deacylated chitin), and starches. These may be generically represented by Formula 1 as follows:

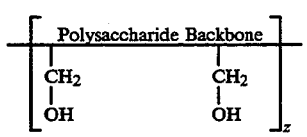
(Formula 1)

In the above formula, only certain hydroxylated sites are shown and z can be any integer representative of the above mentioned hydroxylated polysaccharide substrates. Crosslinked agarose ("SEPHAROSE") is preferred because of its stability when being activated by means of an organic sulfonyl chloride in the presence of a superacylation catalyst such as DMAP.

While the preferred activating agent is tosyl chloride, other aryl or alkyl sulfonyl chlorides such as methane sulfonyl chloride and benzene sulfonyl chloride may be used. As such, they are represented by the formula Cl—SO$_2$—A wherein A can be any suitable alkyl or aryl group such as methyl, ethyl, phenyl or p-tolyl. Preferably A will be p-tolyl such that —SO$_2$—A represents the tosyl group.

In the absence of an activation catalyst the reaction between the organic sulfonyl chloride and the hydroxylated polymer is difficult at best and the degree of activation of hydroxylated carbon atoms is lower due to the relatively lower reactivity of the tosyl group to nucleophilic displacement compared to the tresyl group, for example. However, under more vigorous reaction conditions, i.e., in the presence of an appropriate catalyst such as the 4-dialkylaminopyridines, the reaction is considerably facilitated and the number of activated sites is increased substantially. The alkyl groups of the catalyst may contain from one to three carbon atoms with the methyl group being preferable.

The ligands to which the polyanionic, such as heparin, may be bound can be any suitable polymer having a polyamide backbone with pendent alkyl amines which contain up to five carbon atoms on the pendent alkyl amine chain. Polyamides derived from the polymerization of polyaminocarboxylic acids are suitable, particularly those containing an α-amino group. For example polymers of lysine (α, ε-diaminocaproic acid) and ornithine (α,σ-diaminovaleric acid) are particularly suitable. However, monomers of polyaminocarboxylic acids wherein an amino group is in the β- or γ- position could also be used. Such an polyamide having pendent alkylamine side chains can be represented by Formula 2:

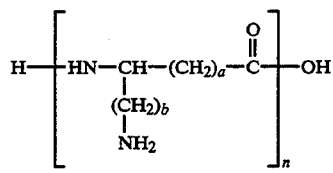
(Formula 2)

where a is an integer of 0, 1 or 2, b is an integer of between 1 and 4 and wherein n is an integer of between about 200 and 750 and which becomes cationic when the terminal amino groups on the side chain become protonated. The ionization of the amino groups depend upon the pH of the medium in which it is contained but will form electrostatic interactions with heparin at a neutral pH. The positive charges per ligand molecule can be adjusted by selecting different molecular different variables of a, b and n and by pH. On a molecular weight basis, the ligand weights will vary between about 35,000 to 80,000 daltons with n being an integer representing between about 200 to 750 monomeric units.

The preferred ligand is poly-L-lysine (PLL). PLL is a polypeptide of the formula:

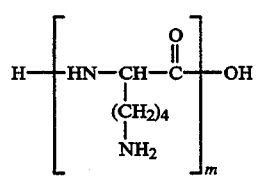
(Formula 3)

wherein m is an integer of between about 200 and 240 and which becomes cationic when the ε-amino groups on the side chain become fully protonated. As stated above, the ionization of the amino groups depends upon the pH of the medium in which it is contained but is known to form electrostatic interactions with heparin at a neutral pH. The positive charges of PLL per molecule can be adjusted by selecting different molecular PLL weights. The molecular weight range of PLL will generally vary between about 40,000 and 50,000.

The reaction of a hydroxylated polysaccharide support (generically represented by Formula 1 where z can be any number of repeating polysaccharide units and wherein the respective hydroxylated moieties do not necessarily represent adjacent hydroxyl groupings) with an organic sulfonyl chloride activating agent, such as tosyl chloride, in the presence of an activation catalyst, such as DMAP may be represented by the following reaction sequence:

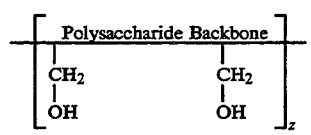
(Formula 1)

ClSO$_2$—A
4-Dialkylamino Pyridine
Catalyst
Non-aqueous Solvent

-continued

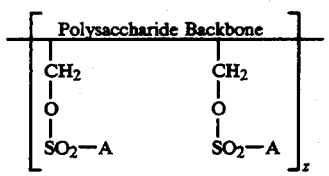
(Formula 4)

Care must be exercised in this part of the preparation of a polycationic support. The efficacy achieved by use of a catalyst such as DMAP when compared to pyridine shows the DMAP to be clearly superior. In fact, the use of DMAP as a tosylation catalyst is so efficient that, when using noncrosslinked supports, care must be exercised that tosylation does not occur to the degree that the support becomes soluble in the solvent. Acetone is a preferred solvent for the activation reaction. However, N-methylpyrrolidone and dimethylformamide may also be used as activation and particularly as tosylation solvents.

The coupling reaction of the sulfonyl chloride activated intermediates of Formula 4 with a polyamide ligand (Formula 2) is carried out in a buffered aqueous solution at an elevated temperature (25° to 60° C.) to covalently link a primary amino group from a pendant alkylamine chain with one or more activated sites in the substrate polymer surface as represented in the following sequence:

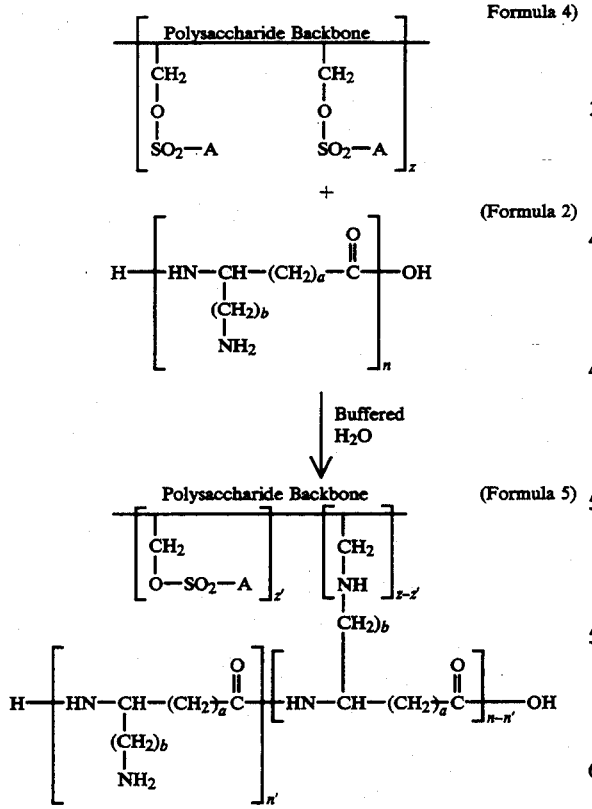

where z-z' represents the number of activated sites reacted with a pendent aminoalkyl group of the ligand and z' represents the activated sites which remain unreacted, n—n' represents the pendent aminoalkyl groups on the polyamide backbone reacting with the activated polysaccharide polymer and n' represents the aminoalkyl groups on the polyamide backbone which can theoretically form polycations for heparin binding purposes.

In Formula 5, any of the amino groups on the pendent alkyl amine chains on the ligand could be involved in the reaction. Two or more amino groups from the same ligand molecule could be bound to the activated support. Also, the degree of derivatization of the activated support with the ligand is a function of many variables such as choice of hydroxylated substrate, activation agent and catalyst used, degree of activation of the substrate, molar ratios of substrate and ligand, reaction conditions, etc.

The final step in preparation of a suitable polycationic support involves the removal of the unreacted sulfonate groups from the ligand derivatized substrate with a suitable agent, i.e. cysteine, Tris buffer, lysine, mercaptoethanol, propyl mercaptan, etc. This reaction sequence may be generally represented as:

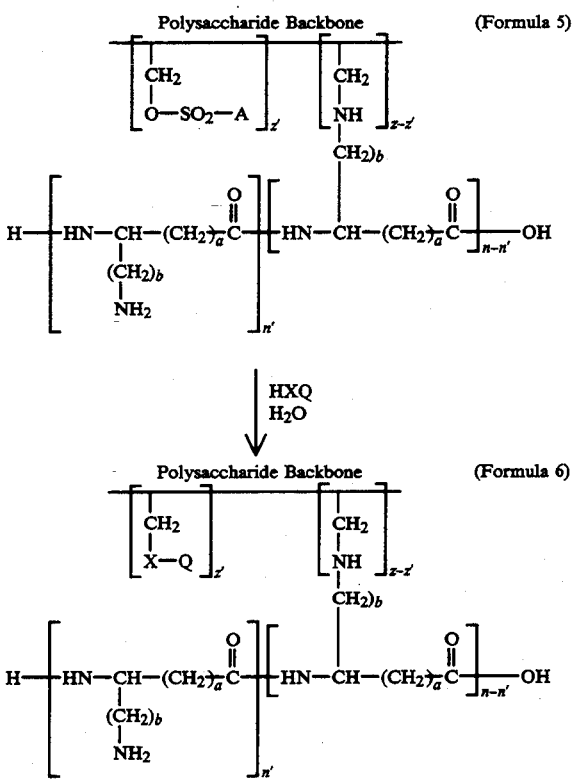

where z-z', n-n' and n' are as described above and z' represents the activated sites which were reacted or capped with the agent HXQ where is X is O, S or NH and Q is the remaining residue of a member selected from the group consisting of mercaptoethanol, Tris buffer, lysine, cysteine and propyl mercaptan not represented by X.

The use of cysteine as a capping agent keeps toxicity at a minimum and also increases the cationic charge on the final polymer product.

The above reaction sequences and Formulas are but representative of the steps to follow and the products which may be synthesized within the scope of the present invention. The basic reaction sequence may be readily adapted by one having ordinary skill in the art to the particular hydroxylated support, organic sulfonyl chloride, activation catalyst and ligand being used.

Crosslinked Sepharose is preferred as the hydroxylated support to be activated by tosyl chloride in the presence of DMAP as the activation catalyst. PLL is the preferred ligand for derivatization of the tosylated crosslinked sepharose and cysteine is the preferred capping agent to remove all reactive sites from the PLL derivatized crosslinked sepharose. The preparation of this product is illustrated by the following examples.

EXAMPLE 1

Dehydration and Tosylation of Agarose (Sepharose 4B-Cl)

Dehydration: A well agitated suspension of crosslinked agarose (Sepharose 4B-Cl) was decanted into a 500 ml graduated cylinder up to the 400 ml mark and the material was degassed by placing it under a vacuum for two minutes while striking the sides of the cylinder sharply with a thick rubber tube. The suspension was then allowed to settle for twenty four (24) hours to provide a compacted bed volume of 336 ml. The average of several experiments proved to be 336±1 ml. The compacted material was next filtered under suction in a Buchner funnel and the graduated cylinder was rinsed with a small amount of 50% (v/v) aqueous acetone. The resulting damp filter cake was transferred to a 2 liter Erlenmeyer flask to which was added 750 ml of 50% (v/v) aqueous acetone (technical grade) forming a suspension which was mechanically stirred at approximately 100 to 150 rpm for 15 min. The material was filtered and the flask rinsed with 100 ml of acetone (in portions). After drying for 5 min. on the Buchner funnel, the Sepharose was returned to the flask and stirred with 750 ml of technical grade acetone for 15 min at 100-150 rpm and filtered. The flask was then rinsed with 100 ml of acetone, and the material dried on the funnel for 5 min. and returned to the flask. This process was repeated two additional times with technical grade acetone and once with reagent grade acetone to produce the dehydrated Sepharose beads, which were then dried on the Buchner funnel for 5 min. and resuspended in 750 ml of reagent grade acetone in a 2 liter round bottom flask.

Tosylation: To the suspension of Sepharose described above, was added 12 g of 98% p-toluenesulfonyl chloride (Aldrich Chemical Co.) and the suspension was stirred 5 min. at 100-150 rpm. To this was added 12 g of 4-dimethylaminopyridine or DMAP (98%, Aldrich Chemical Co.) and stirred continuously for 24 hours at room temperature. After the reaction period, 25 ml of water was added and stirred continuously for 30 minutes followed by the addition of 100 ml of water and stirred for 30 minutes more. Finally, the suspension was poured into 2 liters of water containing 75 ml of concentrated HCl, filtered and the solid washed with one liter of water, once with 250 ml of saturated sodium bicarbonate and two times with one liter of water. A compacted bed volume of 160±1 ml was obtained on settling for 24 hours in degassed water. The material was then stored as a water suspension in the refrigerator.

These reactions may be represented by the following sequence and formulas:

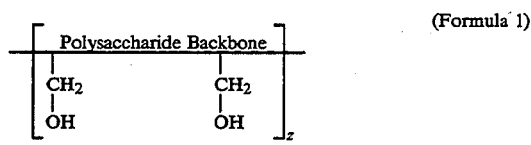
(Formula 1)

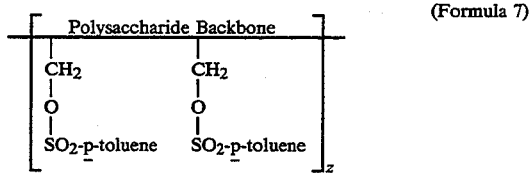
(Formula 7)

EXAMPLE 2

Derivatization of Tosylated Sepharose With Poly-L-Lysine (PLL)

Sodium bicarbonate buffer solution (0.5M) was prepared by dissolving 0.5 mole of sodium bicarbonate (42 g) in approximately 850 ml of water in a one liter volumetric flask. Solid sodium hydroxide added until a pH of 9.5 was obtained. Water was then added to the one liter mark to yield the final solution having a pH of about 9.5. The tosylated sepharose beads prepared in Example 1 (160 ml, filtered and dried 5 min. on the Buchner funnel) were suspended in 100.0 ml of 0.5M bicarbonate buffer (pH 9.5) in a 500 ml round bottom flask and 3.0 g of poly-L-lysine hydrobromide (MW=50,000) were added. This mixture was mechanically stirred at 100-150 rpm in a constant temperature bath at 43°-44° C. for 24 hr. The solid was carefully filtered and the flask rinsed with portions of 150 ml of water. The filtrate was quantitatively transferred to a bottle for future determination of residual poly-L-lysine and the solid air dried on the Buchner funnel for 5 min. A compacted bed volume of 151±2 ml was obtained on settling 24 hr. in degassed water.

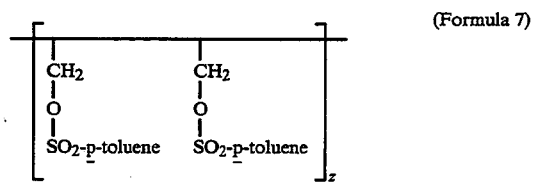
(Formula 7)

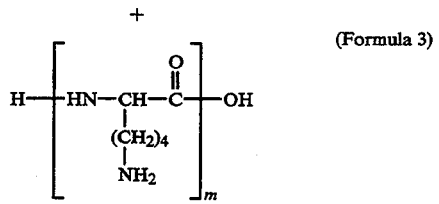
(Formula 3)

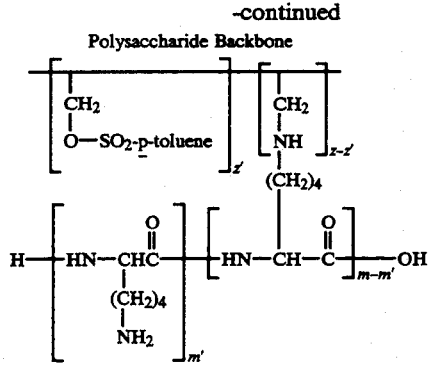

(Formula 8)

where z–z' represents the number of activated sites reacted with a pendent aminoalkyl group of the PLL ligand and z' represents the tosylated sites which remain unreacted, m–m' represents the pendent aminoalkyl groups on the PLL polyamide backbone reacting with the activated polysaccharide polymer and m' represents the aminoalkyl groups on the PLL polyamide backbone which can theoretically form polycations for heparin binding purposes.

EXAMPLE 3

Tosyl Group Capping of PLL Derivatized Sepharose With L-Cysteine

To approximately 50 ml of 0.5M bicarbonate buffer in a 100 ml volumetric flask was added 2.85 g of sodium hydroxide. After the sodium hydroxide was thoroughly dissolved, 6.0 g of L-cysteine hydrochloride was added, the solution was diluted to obtain a solution of 0.5M bicarbonate buffer with a final pH of 9.3. In a 500 ml round bottom was suspended the above product (151 ml), the L-cysteine solution added and the mixture stirred at 43°–44° C. for 24 hours at 100–150 rpm. The final product was suction filtered, washed once with 250 ml of 0.5M bicarbonate buffer and then with one liter of water and stored as a water suspension in a refrigerator. Compacted bed volume was 150±2 ml (24 hr., degassed water).

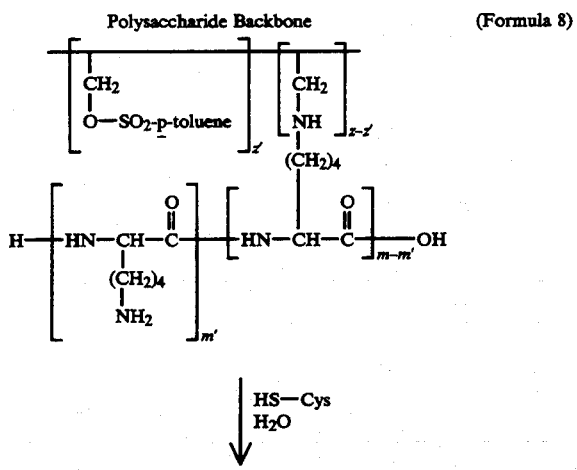

(Formula 8)

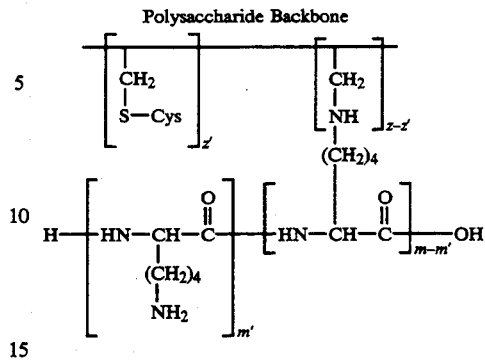

(Formula 9)

where z–z', m–m' and m' are as described above and z' represents the activated sites which were reacted or capped with cysteine.

EXAMPLE 4

To a suspension of 410 mls of tosylated sepharose beads prepared as in Example 1 was added 3694 mg of PLL (minus HBr weight) according to the procedures of Examples 3 and 4. The resulting product was then analyzed to determine the degree of PLL derivatization. The total PLL found bound to the bead gel was 3482 mg. providing for 94.25% (3482/3694) of the PLL being bound. This provided 8.49 mg of PLL per each ml of bead gel.

Polyanions, such as heparin, are removed from fluids, such as blood plasma and whole blood, by bringing these fluids in contact with the polycationic supports prepared as described above. Heparin, as a polyanion, is bound to the polycations by ionic attraction. Heparin can then be released from the support immobilized polycations by treatment with a basic solution, thereby allowing the material to be reused.

The immobilized polycationic materials preferably have as large a surface area as possible to maximize contact between the heparin and the polycationic ligands. The immobilized polycationic surfaces can be in the form of films, beads, honeycombs, fibers, coated surfaces, strands, filaments and the like.

The rate of heparin binding is somewhat dependent on controlling parameters such as blood flow rates, concentration of heparin in blood and exposure time of heparinized blood to the binding substrate. The binding of heparin onto the polycationic surfaces grafted to the polymer surface via the activation process described above seems to depend on the balance of several factors such as the size of the polycation ligand, the degree of ligand derivatization of the substrates, the capping of the activation sites not reacted with the ligand and the like.

The heparin removal from polycationic containing substrates is primarily due to the charge interaction between the polyanionic heparin and the polycations. No hemolysis or clotting is observed in circulating blood, suggesting the such a removal system will not cause adverse effects on blood. The system is also effective in removing heparin from aqueous solutions other than blood.

EXAMPLE 5

Absorption of Heparin by Derivatized Sepharose with Immobilized PLL

One hundred ml samples of heparin contained in a buffer at heparin concentrations of approximately 2, 4 and 6 μ/ml were stirred with 0.38 ml of the gel obtained from Example 3 at a constant temperature of 20° C with constant agitation. The following table shows the heparin removal at the three concentrations as a function of time. The concentration of heparin was assayed with Azure dye (2.0) with an activity assay of 3.3.

TABLE 1

| Time (min) | Initial Heparin Concentration μ/ml | | |
|---|---|---|---|
| | 6.0 | 4.0 | 2.0 |
| | Measured Concentration μ/ml | | |
| 0 | 5.99 | 4.31 | 2.14 |
| 10 | 2.66 | 1.25 | 0.39 |
| 20 | 1.81 | 0.69 | 0.20 |
| 30 | 1.41 | 0.53 | 0.00 |

Table 2 shows the same results in terms of percent heparin reduction at ten minute intervals from that measured at zero time.

TABLE 2

| Time (min) | Assayed Heparin Concentration μ/ml | | |
|---|---|---|---|
| | 5.99 | 4.31 | 2.14 |
| | Percent (%) Reduction | | |
| 0 | 00.0 | 00.0 | 00.0 |
| 10 | 55.6 | 71.0 | 81.8 |
| 20 | 69.8 | 84.0 | 90.6 |
| 30 | 76.5 | 87.7 | 100 |

While the invention has been described and illustrated with reference to certain preferred embodiments thereof, those skilled in the art will appreciate that various modifications, changes, omissions, and substitutions can be made without departing from the spirit of the invention. Heparin is but representative of polyanions which may be removed and or concentration controlled by means of the invention and blood or blood plasma is but representative of polyanion containing fluids which may be treated. It is intended, therefore, that the invention be limited only by the scope of the following claims.

We claim:

1. A method for producing a ligand-derivatized and capped polymer comprising:
   (a) reacting a support polymer containing free hydroxyl groups selected from the group consisting of carbohydrates, diol-silica, glycophase-glass, and hydroxyethyl methacrylate gels with an alkyl or aryl sulfonyl chloride in the presence of a di($C_1$-$C_3$)-alkylaminopyridine to form an activated support;
   (b) reacting the activated support with a polymer having a polyamide backbone with pendent alkyl amine groups to form C—N bonds between activated carbons from the hydroxylated polymer and amine groups from the polymeric polyamide, said polymeric polyamide having the formula:

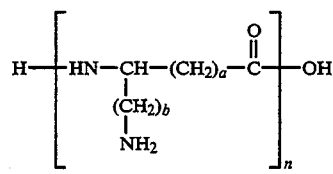

where a is an integer of 0, 1, or 2; b is an integer of 1 to 4; and n is an integer of between about 200 and 750; and
   (c) removing unreacted activated sites on the hydroxylated polymer by reaction with an effective amount of a capping agent selected from the group consisting of mercaptoethanol, Tris buffer, lysine, cysteine, and propyl mercaptan.

2. The method of claim 1 wherein said polymer having a polyamide backbone with pendent alkyl amine groups is polycationic when the terminal amino groups on the side chains are protonated.

3. The method of claim 2 wherein said polymer having a polyamide backbone with pendent alkyl amine groups is poly-L-lysine.

4. The method of claim 2 wherein the capping agent is cysteine.

5. The method of claim 1 wherein the support containing free hydroxyl groups is a carbohydrate.

6. The method of claim 5 wherein the carbohydrate is agarose or cellulose.

7. The method of claim 6 wherein the agarose is crosslinked agarose.

8. The method of claim 1 wherein, the alkyl or aryl sulfonyl chloride is selected from the group consisting of methane-, ethane-, benzene-, and p-toluene-sulfonyl chlorides.

9. The method of claim 8 wherein the alkyl or aryl sulfonyl chloride is p-toluene-sulfonyl chloride.

10. The method of claim 9 wherein the di($C_1$-$C_3$)-alkylaminopyridine is dimethylaminopyridine.

11. The method of claim 10 wherein said support group is a carbohydrate and said polymer having a polyamide backbone with pendent alkyl amine groups is poly-L-lysine.

12. The method of claim 11 wherein said support group is crosslinked agarose.

13. The method of claim 12 wherein said capping agent is cysteine.

14. A ligand-derivatized and capped polymer produced by:
   (a) reacting a support polymer containing free hydroxyl groups selected from the group consisting of carbohydrates, diol-silica, glycophase-glass, and hydroxyethyl methacrylate gels with an alkyl or aryl sulfonyl chloride in the presence of a di($C_1$-$C_3$)-alkylaminopyridine to form an activated support;
   (b) reacting the activated support with a polymer having a polyamide backbone with pendent alkyl amine groups to form C—N bonds between activated carbons from the hydroxylated polymer and amine groups from the polymeric polyamide, said polymeric polyamide having the formula:

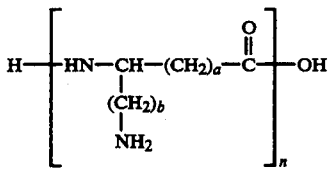

where a is an integer of 0, 1, or 2; b is an integer of 1 to 4; and n is an integer of between about 200 and 750; and (c) removing unreacted activated sites on the hydroxylated polymer by reaction with an effective amount of a capping agent selected from the group consisting of mercaptoethanol, Tris buffer, lysine, cysteine, and propyl mercaptan.

15. The polymer produced according to claim 14 wherein said polymer having a polyamide backbone with pendent alkyl amine groups is polycationic when the terminal amino groups on the side chains are protonated.

16. The polymer produced according to claim 15 wherein said polymer having a polyamide backbone with pendent alkyl amine groups is poly-L-lysine.

17. The polymer produced according to claim 15 wherein the capping agent is cysteine.

18. The polymer produced according to claim 16 wherein the support containing free hydroxyl groups is a carbohydrate.

19. The polymer produced according to claim 18 wherein the carbohydrate is agarose or cellulose.

20. The polymer produced according to claim 19 wherein the agarose is crosslinked agarose.

21. The polymer produced according to claim 16 wherein, the alkyl or aryl sulfonyl chloride is selected from the group consisting of methane-, ethane-, benzene-, and p-toluene-sulfonyl chlorides.

22. The polymer produced according to claim 21 wherein the alkyl or aryl sulfonyl chloride is p-toluene-sulfonyl chloride.

23. The polymer produced according to claim 22 wherein the di(C$_1$–C$_3$)- alkylaminopyridine is dimethylaminopyridine.

24. The polymer produced according to claim 23 wherein said support group is a carbohydrate and said polymer having a polyamide backbone with pendent alkyl amine groups is poly-L-lysine.

25. The polymer produced according to claim 24 wherein said support group is crosslinked agarose.

26. The polymer produced according to claim 25 wherein said capping agent is cysteine.

27. A method for removing a polyanion from a polyanion-containing fluid which comprises contacting the fluid with the ligand-derivatized and capped polymer produced by:

(a) reacting a support polymer containing free hydroxyl groups selected from the group consisting of carbohydrates, diol-silica, glycophase-glass, and hydroxyethyl methacrylate gels with an alkyl or aryl sulfonyl chloride in the presence of a di(C-1–C$_3$)-alkylaminopyridine to form an activated support;

(b) reacting the activated support with a polymer having a polyamide backbone with pendent alkyl amine groups to form C—N bonds between activated carbons from the hydroxylated polymer and amine groups from the polymeric polyamide, said polymeric polyamide having the formula:

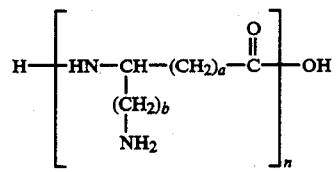

where a is an integer of 0, 1, or 2; b is an integer of 1 to 4; and n is an integer of between about 200 and 750; and (c) removing unreacted activated sites on the hydroxylated polymer by reaction with an effective amount of a capping agent selected from the group consisting of mercaptoethanol, Tris buffer, lysine, cysteine, and propyl mercaptan.

28. The method according to claim 27 wherein said polymer having a polyamide backbone with pendent alkyl amine groups is polycationic when the terminal amino groups on the side chains are protonated.

29. The method according to claim 28 wherein said polymer having a polyamide backbone with pendent alkyl amine groups is poly-L-lysine.

30. The method according to claim 28 wherein the capping agent is cysteine.

31. The method according to claim 28 wherein the support containing free hydroxyl groups is a carbohydrate.

32. The method according to claim 31 wherein the carbohydrate is agarose or cellulose.

33. The method according to claim 31 wherein the agarose is crosslinked agarose.

34. The method according to claim 31 wherein, the alkyl or aryl sulfonyl chloride is selected from the group consisting of methane-, ethane-, benzene-, and p-toluene-sulfonyl chlorides.

35. The method according to claim 34 wherein the alkyl or aryl sulfonyl chloride is p-toluene-sulfonyl chloride.

36. The method according to claim 35 wherein the di(C$_1$–C$_3$)-alkylaminopyridine is dimethylaminopyridine.

37. The method according to claim 36 wherein said support group is a carbohydrate and said polymer having a polyamide backbone with pendent alkyl amine groups is poly-L-lysine.

38. The method according to claim 37 wherein said support group is crosslinked agarose.

39. The method according to claim 38 wherein said capping agent is cysteine.

40. The method according to claim 37 wherein said polyanion is heparin.

41. The method according to claim 40 wherein said polyanion containing fluid is whole blood.

42. The method according to claim 40 wherein said polyanion containing fluid is blood plasma.

* * * * *